(12) United States Patent
Li et al.

(10) Patent No.: US 7,828,875 B2
(45) Date of Patent: Nov. 9, 2010

(54) MEMBRANES FOR HIGHLY SELECTIVE SEPARATIONS

(75) Inventors: Shiguang Li, Boulder, CO (US); Sara A. Arvidson, Fayetteville, NC (US); John L. Falconer, Boulder, CO (US); Richard D. Noble, Boulder, CO (US)

(73) Assignee: The Regents of the University of Colorado, Denver, CO (US)

( * ) Notice: Subject to any disclaimer, the term of this patent is extended or adjusted under 35 U.S.C. 154(b) by 1132 days.

(21) Appl. No.: 11/194,515

(22) Filed: Aug. 1, 2005

(65) Prior Publication Data

US 2006/0079725 A1 Apr. 13, 2006

Related U.S. Application Data

(60) Provisional application No. 60/598,733, filed on Aug. 3, 2004.

(51) Int. Cl.
*B01D 59/12* (2006.01)
(52) U.S. Cl. .............. 95/51; 95/45; 502/4; 502/86
(58) Field of Classification Search ............. 95/51, 95/45; 502/4, 86
See application file for complete search history.

(56) References Cited

U.S. PATENT DOCUMENTS

| | | | |
|---|---|---|---|
| 3,404,086 A | 10/1968 | Plank et al. |
| 3,644,200 A | 2/1972 | Young |
| 4,414,005 A | 11/1983 | De Bievre et al. |
| 4,440,871 A | 4/1984 | Lok et al. |
| 4,775,396 A | 10/1988 | Rastelli et al. |
| 5,100,596 A | 3/1992 | Haag et al. |
| 5,124,289 A | 6/1992 | Martin et al. |
| 5,143,876 A | 9/1992 | Chang et al. |
| 5,248,647 A | 9/1993 | Barger |
| 5,362,522 A | 11/1994 | Barri et al. |
| 5,464,798 A | 11/1995 | Jia et al. |
| 5,557,030 A | 9/1996 | Markovs et al. |
| 5,567,664 A | 10/1996 | Barri et al. |
| 6,043,177 A | 3/2000 | Falconer et al. |
| 6,051,745 A | 4/2000 | Wu et al. |
| 6,051,746 A | 4/2000 | Sun et al. |
| 6,074,457 A | 6/2000 | Athonis et al. |
| 6,140,263 A | 10/2000 | Anstett et al. |

(Continued)

FOREIGN PATENT DOCUMENTS

JP 62-052123 3/1987

(Continued)

OTHER PUBLICATIONS

Aoki et al. (1998) "Gas Permeation Properties of A-Type Zeolite Membrane Formed on Porous Substrate by Hydrothermal Synthesis," *AlChe J.* 141:197-205.

(Continued)

*Primary Examiner*—Walter D Griffin
*Assistant Examiner*—Renee Robinson
(74) *Attorney, Agent, or Firm*—Greenlee Sullivan PC

(57) ABSTRACT

The present invention provides modified molecular sieve membranes with improved $CO_2/CH_4$ separation selectivity and methods for making such membranes. The molecular sieve membranes are modified by adsorption of a modifying agent, such as ammonia, within and/or on the membrane.

10 Claims, 11 Drawing Sheets

U.S. PATENT DOCUMENTS

| | | | |
|---|---|---|---|
| 6,193,784 | B1 | 2/2001 | Yazawa et al. |
| 6,503,294 | B2 | 1/2003 | Yoshikawa et al. |
| 6,734,129 | B2 | 5/2004 | Lai et al. |
| 6,756,516 | B2 | 6/2004 | Mees et al. |
| 6,767,384 | B1 | 7/2004 | Vu et al. |
| 6,897,180 | B2 | 5/2005 | Mees et al. |
| 2003/0089227 | A1* | 5/2003 | Hasse et al. ................... 95/45 |
| 2003/0149321 | A1* | 8/2003 | Mees et al. ................ 585/640 |
| 2003/0220188 | A1* | 11/2003 | Marand et al. ............... 502/60 |
| 2005/0204916 | A1 | 9/2005 | Falconer et al. |
| 2007/0265484 | A1 | 11/2007 | Li et al. |
| 2008/0216650 | A1 | 9/2008 | Falconer et al. |
| 2010/0102001 | A1 | 4/2010 | Falconer et al. |
| 2010/0116130 | A1 | 5/2010 | Carreon et al. |

FOREIGN PATENT DOCUMENTS

| | | | |
|---|---|---|---|
| JP | 04-022415 | | 1/1992 |
| JP | 04022415 | A * | 1/1992 |
| JP | 2000-508231 | | 7/2000 |
| JP | 2001 146416 | | 5/2001 |
| JP | 2001-146416 | A | 5/2001 |
| JP | 2005-503259 | | 2/2005 |
| RU | 2174044 | | 9/2001 |
| RU | 2179064 | | 2/2002 |
| WO | WO94/25152 | | 11/1994 |
| WO | WO 97/37752 | | 10/1997 |
| WO | WO97/37752 | A | 10/1997 |
| WO | WO 03/26775 | | 4/2003 |
| WO | WO 2008/106647 | | 9/2008 |

OTHER PUBLICATIONS

Bakker et al. (1996) "Permeation Characteristics of a Metal-Supported Silicalite-1 Zeolite Membrane," *J. Membrane Sci.* 117:57-78.
Breck, D.W. (1974) *Zeolite Molecular Sieves*, Krieger Publishing Company. Malabar, Florida, pp. 460-465,498-503,570-573.
Buchholz et al. (2004) "Sequential Steps of Ammoniation of the Microporous Silicoaluminophosphates H-SAPO-34 and H-SAPO-37 Investigated by In Situ CF MAS NMR Spectroscopy," *J. Phys. Chem. B* 108:3107-3113 (February).
Dyer et al. (1988) *An Introduction to Zeolite Molecular Sieves*, John Wiley and Sons, New York, pp. 1-3,12-15,20-25,36-37,54,57,118-124.
Guan et al. (2002) "Separation of Nitrogen From Oxygen Using A Titanosilicate Membrane Prepared on a Porous α-Alumina Support Tube," *Sep. Sci. Technol.* 37(5):1031-1039.
Gues et al. (1992) "Synthesis and Characterization of Zeolite (MFI) Membranes on Porous Ceramic Supports," *J. Chem. Soc. Faraday Trans.* 88:3101-3109.
Gump et al. (2001) "Aromatic Permeation Through Crystalline Molecular Sieve Membranes," *Ind. Engr. Chem. Res.* 40(2):565-577.
Hedlund et al. (2002) "High-Flux MFI Membranes," *Micro. Meso. Mater.* 52:179-189.
International Search Report Corresponding to International Application No. PCT/US05/027530, Mailed Oct. 10, 2006.
Jhung et al. (2003) "Selective Formation of SAPO-5 and SAPO-34 Molecular Sieves with Microwave Irradiation and Hydrothermal Heating," *Micro. Meso. Mater.* 64:33-39.
Jia et al. (1993) "Ceramic Zeolite Composite Membranes," *J. Membr. Sci.* 82:15-26.
Kärger et al. (1992) *Diffusion in Zeolites*, John Wiley and Sons, New York, pp. 9-10.
Keizer et al. (1998) "Two Component Permeation Through Thin Zeolite MFI Membranes," *J. Memb. Sci.* 147:159-172.
Kusakabe et al. (1997) Formation of a Y-Type Membrane on a Porous α-Alumina Tube for Gas Separation, *Ind. Eng. Chem. Res.* 36:649-655.
Li et al. (2002) "ZSM-11 Membranes: Characterization and Pervaporation Performance for Alcohol/Water Mixtures." *AIChE J.* 48:269-278 (February).
Li et al. (2004) "SAPO-34 Membranes for $CO_2/CH_4$ Separation," *J. Memb. Sci.* 241:121-135.
Li et al. (2004) "Effects of Impurities on $CO_2/CH_4$ Separations Through SAPO-34 Membranes," *J. Membr. Sci.* 251:59-66.
Lixiong et al. (1997) "Synthesis of SAPO-34/Ceramic Composite Membranes," *Stud. Surf. Sci. Catl.* 105:2211-2215.
Masuda et al. (1995) "Preparation of an A-Type Zeolite Film on the Surface of an Alumina Ceramic Filter," *Microporous Mat.* 3:565-571.
Masuda et al. (1994) "Preparation of a Dense ZSM-5 Zeolite Film on the Outer of an Alumina Ceramic Filter," *Appl. Catal.* 111:143-150.
Mees et al. (2003) "Improvement of the Hydrothermal Stability of SAPO-34," *Chem. Commun.* 1:44-45.
Mees et al. (2002) "Electronic Supplementary Information (ESI) on the Synthesis Procedure," *Supp. Material for Chem. Commun.*
Meriaudeau et al. (1997) "SAPO-11, SAPO-31, and SAPO-41 Molecular Sieves: Synthesis, Characterization, and Catalytic Properties in *n*-Octane Hydroisomerization," *J. Catalysis* 169:55-66.
Poshusta et al. (1998) "Synthesis and Permeation Properties of SAPO-34 Tubular Membranes," *Ind. Eng. Chem. Res.* 37:3924-3929.
Poshusta et al. (2000) "Separation of Light Gas Mixtures Using SAPO-34 Membranes," *AlChe J.* 46(4):779-789 (April).
Poshusta et al. (1999) "Temperature and Pressure Effects on $CO_2$ and $CH_4$ Permeation Through MFI Zeolite Membranes," *J. Membr. Sci.* 160:115-125.
Poshusta et al. (2001) "Characterization of SAPO-34 Membranes by Water Absorption," *J. Membr. Sci.* 186:25-40.
Prakash et al. (1994) "Synthesis of SAPO-34: High Silicon Incorporation in the Presence of Morpholine as Template," *J. Chem. Soc. Faraday Trans.* 90(15):2291-2296.
Recipe for SAPO-34, http://www.iza-synthesis.org/Recipies/SAP0-34.html, Accessed Jan. 15, 2004.
Sano et al. (1992) Synthesis and Characterization of Polycrystalline SAPO-5 Film, *J. Mol. Cat.* 77:L19-L26.
Sherman, J.D. (1999) "Synthetic Zeolites and Other Microporous Oxide Molecular Sieves," *Proc. Natl. Acad. Sci. USA* 96:3471-3478 (March).
Szostak, R. (1998) "Synthesis of Molecular Sieve Phosphates,"in, "Recent Advances in the Understanding of Zeolite Synthesis," in, *Molecular Sieves, Science and Techonology*, Karge et al. Eds., Springer-Verlag, Berlin pp. 161-165.
Thompson, R.W. (1998) "Recent Advances in the Understanding of Zeolite Synthesis," in, *Molecular Sieves, Science and Technology*, Karge et al., Eds., Springer-Verlag, Berlin, pp. 19-31.
Tomita et al. (2004) "Gas Separation Characteristics of DDR Type Zeolite Membrane," *Micropor. Mesopor. Mater.* 68:71-75.
Tsai et al. (1998) Well-Aligned SAPO-5 Membrane: Preparation and Characterization, *Micropor. Mesopor. Mat.* 22:333-341.
Tuan et al. (2002) "Separating Organics From Water by Pervaporation with Isomorphously-Substituted MFI Zeolite Membranes," *Mem. Sci.* 196:111-123.
Van der Broeke et al. (1999) "Transport and Separation Properties of a Silicalite-1 Membrane, I. Operating Conditions," *Chem. Eng. Sci.* 54:245-258.
Vomscheid et al. (1995) "Reversible Interaction of $NH_3$ with the Framework of Template-Free Zeolite-Type SAPO-34," *J. Chem. Soc. Faraday Trans.* 91(18):3281-3284.
Weh et al. (2002) "Change of Gas Permeation by Photoinduced Switching of Zeolite-Azobenzene Membranes of Type MFI and FAU," *Micropor. Mesopor. Mater.* 54:15-26.
Weh et al. (2002) "Permeation of Single Gases and Gas Mixtures Through Faujasite-Type Molecular Sieve Membranes," *Micropor. Mesopor. Mater.* 54:27-36.
Yan et al. (1995) "Zeolite ZSM-5 Membranes Grown on Porous α-$Al_2O_3$," *JCS Chem. Commun.* 2:227-228.
Zecchina et al. (1997) "Vibrational Spectroscopy of $NH_4$ + Ions in Zeolitic Materials: An IF Study," *J. Phys. Chem. B* 101:10128-10135.
Zhu et al. (1999) "Shape Selectivity in the Adsorption of Propane/Propene on the All-Silica DD3r," *Chem. Commun.* 1453-2454.
Supplemental European Search Report, Corresponding to European Application No. EP 05 77 8609, Completed Mar. 25, 2008.

* cited by examiner

MEMBRANES FOR HIGHLY SELECTIVE SEPARATIONS

CROSS-REFERENCE TO RELATED APPLICATIONS

This application claims the benefit of U.S. Provisional Application No. 60/598,733, filed Aug. 3, 2004, which is incorporated by reference in its entirety herein.

BACKGROUND OF THE INVENTION

This invention is in the field of zeolite-type membranes whose selectivity is improved by adsorption of a modifying agent within and/or on the membrane. Useful modifying agents include ammonia.

Zeolites are largely composed of Si, Al and O and have a three-dimensional microporous crystal framework structure largely of $[SiO_4]^{4-}$ and $[AlO_4]^{5-}$ tetrahedral units. To balance negative charge due to the incorporation of Al atoms in the framework, cations are incorporated into the cavities and channels of the framework. The cages, channels and cavities created by the crystal framework can permit separation of mixtures of molecules based on their effective sizes.

Different zeolites may have different Si/Al ratios and the tetrahedra can also be isostructurally substituted by other elements such as B, Fe, Ga, Ge, Mn, P, and Ti. In an extreme case, zeolite molecular sieves may have a Si/Al ratio approaching infinity. Silica molecular sieves do not have a net negative framework charge, exhibit a high degree of hydrophobicity, and have no ion exchange capacity. Silicalite-1, and silicalite-2, and Deca-dodecasil 3R (DD3R) are examples of silica molecular sieves.

Aluminophosphate (AlPO) molecular sieves are largely composed of Al, P and O and have three-dimensional microporous crystal framework structure largely of $[PO_4]^{3-}$ and $[AlO_4]^{5-}$ tetrahedral units. Silicoaluminophosphate (SAPO) molecular sieves are largely composed of Si, Al, P and O and have a three-dimensional microporous crystal framework structure largely of $[PO_4]^{3-}$, $[AlO_4]^{5-}$ and $[SiO_4]^{4-}$ tetrahedral units. Molecular sieve framework structures are discussed in more detail by Baerlocher et al. (Baerlocher, Ch., et al., 2001, Atlas of Framework Structures Types, 5$^{th}$ revised ed., Elsevier, Amsterdam).

Molecular sieve membranes have been proposed for use in separating gas mixtures. Several types of molecular sieve membranes have been tested for separation of mixtures of $CO_2$ and $CH_4$, including FAU zeolite membranes (Kusakabe, K. et al. 1997, Ind. Eng. Chem. Res., 36, 649; Weh, K. et al., 2002, Micropor. Mesopor. Mater. 54, 47), MFI zeolite membranes (Van der Broeke, L. J. P. et al., 1999, Chem. Eng. Sci., 54, 259; Poshusta, J. C. et al., 1999, J. Membr. Sci., 160, 115), SAPO-34 membranes (Poshusta, J. C. et al., 1998, Ind. Eng. Chem. Res., 37, 3924; Poshusta, J. C. et al., 2000, AlChE Journal., 46(4), 779), LTA zeolite membranes (Aoki K. et al., 1998, J. Membr. Sci., 141, 197), ETS-4 zeolite membranes (Guan, G. et al., 2002, Sep. Sci. Technol., 37, 1031), and DD3R membranes (Tomita, T. et al., Micropor. Mesopor. Mater., 2004, 68, 71-75). Tomita et al. reported a $CO_2/CH_4$ separation selectivity of 220 for a DD3R membrane with a 50/50 gas mixture at 301K. Poshusta et al. (2000, supra) reported a $CO_2/CH_4$ separation selectivity of 36 for a SAPO-34 membrane with a 50/50 gas mixture at 300 K. Falconer et al. (U.S. patent application Ser. No. 10/805,183) reported $CO_2/CH_4$ separation selectivities in excess of 60 for a SAPO-34 membrane with a 50/50 gas mixture at 297 K and a 138 KPa pressure drop. Poshusta et al. (1999, supra) reported a $CO_2/CH_4$ separation selectivity of 5.5 for an H-ZSM-5 (MFI structure) membrane with a 50/50 gas mixture at 301K.

Adsorption of ammonia and other compounds on molecular sieves has been reported. Zeolites have been treated with ammonia for the purposes of measuring zeolite acidity. Zeolite acidity is measured from desorption of sorbed ammonia (Dyer, A., *An Introduction to Molecular Sieves*, 1988, John Wiley and Sons, New York, p. 124). SAPOs have also been treated with ammonia to measure acidic site population. U.S. Pat. No. 5,248,647, to Barger et al., reports measuring the acidic site population of silicoaluminophosphates after calcination by contacting the silicoaluminophosphate with a mixture of ammonia and helium and then desorbing the ammonia.

Treatment of metallophosphate molecular sieves with ammonia has been reported to stabilize the molecular sieves. U.S. Patent Publication 2003/0149321A1 to Mees at al. and Mees et al. (Mees, F. D. P, et al. 2003, Chem. Commun., 1, pp 44-45) report stabilization of metalloaluminophosphate molecular sieves, including SAPO 34, through treatment with ammonia. Mees et al. report that the ammonia is chemisorbed to acid catalytic sites of the metalloaluminophosphate molecular sieve. Buchholz et al. report a two step adsorption process for SAPO-34 and SAPO-37 (Buchholz et al., 2004, J. Phys. Chemistry, Vol. 108, pp 3107-3113). As reported, the first step consists of an adsorption of ammonia exclusively at Bronsted acidic bridging OH groups (SiOHAl) leading to the formation of ammonium ions ($NH_4$ form). The second ammoniation step, which was reported to occur at higher ammonia coverage, consists of a coordination of ammonia molecules to framework Al atoms.

Mees et al. (U.S. Pat. No. 6,756,516) also report stabilization of metalloaluminophosphate molecular sieves by treatment with one or more nitrogen containing compounds selected from the group consisting of amines, monocyclic heterocyclic compounds, organonitrile compounds and mixtures thereof so that the nitrogen containing compound is chemisorbed and/or physisorbed with the molecular sieve.

U.S. Pat. No. 6,051,746, to Sun et al., reports modification of small pore molecular sieve catalysts by adsorption of polynuclear aromatic heterocyclic compounds onto the catalyst. The modified catalysts were reported to have increased selectivity to olefins. The modifiers comprise polynuclear aromatic heterocyclic compounds with at least three interconnected ring structures having at least one nitrogen atom as a ring substituent, each ring structure having at least five ring members and quaternary salts thereof.

Ammonium cation exchange of zeolites is also known to the art (Dyer, A., *An Introduction to Molecular Sieves*, 1988, John Wiley and Sons, New York, p. 121). The ammoniated zeolites can then be calcined to produce the hydrogen form of the zeolite.

U.S. Pat. No. 6,051,745 reports nitridation of silicoaluminophosphates which can be achieved with mixtures of ammonia and hydrogen.

SUMMARY OF THE INVENTION

The present invention provides modified molecular sieve membranes with improved separation selectivity for gas mixtures and methods for making and using such membranes. The molecular sieve membranes are modified by adsorption of a modifying agent, such as ammonia, within and/or on the membrane. In an embodiment, the modified molecular sieve membranes are supported membranes. In an embodiment, the modified molecular sieve membranes of the invention have improved $CO_2/CH_4$ selectivity.

The separation of $CO_2$ from $CH_4$ is important in natural gas processing because $CO_2$ reduces the energy content of natural gas. Many natural gas wells contain high concentrations of $CO_2$ (as high as 70%), and most of this $CO_2$ must be removed before the natural gas is shipped and used. To increase the flux across the membrane, it is desirable to use a relatively high pressure differential across the membrane. In industrial gas separation processes, the pressure drop across the membrane can be several MPa. For example, in the natural gas industry the transmembrane pressure drop is about 6 MPa. Polymeric membranes are currently used for $CO_2$ removal in some cases with low $CO_2$ pressures. High partial pressures of $CO_2$ plasticize polymers, and thus limit the use of polymeric membranes for $CO_2/CH_4$ separation.

The modified molecular sieve membrane can be a SAPO-34 membrane. The modified molecular sieve membrane can also be a ZSM-5 membrane or another type of molecular sieve membrane.

SAPO-34 membranes are inorganic membranes which have superior thermal, mechanical and chemical stability, good erosion resistance, and high pressure stability compared to conventional polymeric membranes. SAPO-34 modified with $NH_3$ can have improved $CO_2/CH_4$ separation selectivity as compared to unmodified SAPO-34 membranes. In an embodiment, the improvement in the $CO_2/CH_4$ separation selectivity is an increase of at least 3 orders of magnitude. In an embodiment, the invention provides a supported membrane comprising a porous support and ammoniated SAPO-34 crystals which form a layer on at least one side of the support; wherein the $CO_2/CH_4$ separation selectivity of the membrane is greater than about 42,000 at a temperature between about 297 K and about 323 K, a pressure differential across the membrane between about 2.3 MPa and about 3.0 MPa, and a $CO_2$ concentration between about 25 mol % and about 70 mol %.

In an embodiment, the invention provides a method for treating a molecular sieve membrane to increase its separation selectivity, which comprises:
 a. providing a molecular sieve membrane; and
 b. adsorbing a modifying agent within the membrane, on the membrane, or both on and within the membrane.

In an embodiment, the method improves the $CO_2/CH_4$ selectivity of the membrane. In an embodiment, the modifying agent is ammonia.

In an embodiment, the invention provides a method for separating a first gas component from a gas mixture containing at least a first and a second gas component, the method comprising the steps of:
a) providing a modified molecular sieve membrane, the membrane having a feed and a permeate side, being selectively permeable to the first gas component over the second gas component and being modified by adsorption of a modifying agent;
b) applying a feed stream including the first and the second gas components to the feed side of the membrane;
c) providing a driving force sufficient for permeation of the first gas component through the membrane, thereby producing a permeate stream enriched in the first gas component from the permeate side of the membrane.

The modifying agent can be ammonia. The modified membrane can be an ammoniated SAPO-34 membrane used for separation of $CO_2$ from $CH_4$.

BRIEF DESCRIPTION OF THE DRAWINGS

FIG. 1A shows the surface, while FIG. 1B shows a cross sectional view.

DETAILED DESCRIPTION

Figure 1A:
FIGS. 1A and 1B show SEM photos of a SAPO-34 membrane prior to modification.

In general, the terms and phrases used herein have their art-recognized meaning, which can be found by reference to standard texts, journal references and contexts known to those skilled in the art. The following definitions are provided to clarify their specific use in the context of the invention.

As used herein, a zeolite-type material is a molecular sieve material. A molecular sieve material has a microporous crystal framework structure of tetrahedral units having a cation in tetrahedral cooordination with four oxygens. The tetrahdra are assembled together such that the oxygen at each tetrahedral corner is shared with that in another tetrahedron. For zeolites, the cation is $Al^{3+}$ or $Si^{4+}$. As used herein, "microporous" refers to pore diameters less than about 2 nanometers.

Molecular sieves can be classified as small, medium, or large-pore molecular sieves based on the size of the largest oxygen rings in the structure. Crystalline SAPO-5 has the AFI structure which contains rings of 12 oxygen atoms, 6 oxygen atoms, and 4 oxygen atoms. SAPO-5 is typically considered a large-pore molecular sieve. In contrast, crystalline SAPO-11 has the AEL structure which contains rings of 10 oxygen atoms, 6 oxygen atoms, and 4 oxygen atoms. SAPO-11 is typically considered a medium-pore molecular sieve. Structures where the largest ring contains 8 or fewer oxygen atoms are typically considered small-pore molecular sieves. Small pore molecular sieves include zeolite A, silicoaluminophosphate (SAPO)-34, and Deca-dodecasil 3R. Medium pore molecular sieves include ZSM-5, ZSM-11, and SAPO-11. Large-pore molecular sieves include SAPO-5 and SAPO-37.

Gas Transport through Molecular Sieve Membranes

Transport of gases through a zeolite-type or molecular sieve membrane can be described by several parameters. As used herein, a membrane is a semi-permeable barrier between two phases that is capable of restricting the movement of molecules across it in a very specific manner. As used herein, the flux, $J_i$, through a membrane is the number of moles of a specified component i passing per unit time through a unit of membrane surface area normal to the thickness direction. The permeance or pressure normalized flux, $P_i$, is the flux of component i per unit transmembrane driving force. For a diffusion process, the transmembrane driving force is the gradient in chemical potential for the component (Kärger, J. Ruthven, D. M., Diffusion in Zeolites, John Wiley and Sons: New York, 1992, pp. 9-10). The selectivity of a membrane for components i over j, $S_{i/j}$ is the permeance of component i divided by the permeance of component j. The ideal selectivity is the ratio of the permeances obtained from single gas permeation experiments. The actual selectivity (also called separation selectivity) for a gas mixture may differ from the ideal selectivity.

For two gas components i and j, a separation selectivity $S_{i/j}$ greater than one implies that the membrane is selectively permeable to component i. If a feedstream containing both components is applied to one side of the membrane (the feed side), the permeate stream exiting the other side of the membrane (the permeate side) will be enriched in component i and depleted in component j. The greater the separation selectivity, the greater the enrichment of the permeate stream in component i.

Transport of gases through zeolite pores can be influenced by several factors. As used herein, "zeolite pores" are pores formed by the crystal framework of a zeolite-type material. A model proposed by Keizer et al. (J. Memb. Sci., 1998, 147, p. 159) has previously been applied to SAPO-34 membranes (Poshusta et al., AlChE Journal, 2000, 46(4), pp 779-789). This model states that both molecular sizes relative to the zeolite pore and the relative adsorption strengths determine the faster permeating species in a binary mixture. This gives rise to three separation regimes where both components are able to diffuse through the molecular sieve pores. In the first region, both molecules have similar adsorption strengths, but one is larger and its diffusion is restricted due to pore walls. In the first region, the membrane is selective for the smaller molecule. In region 2, both molecules have similar kinetic diameters, but one adsorbs more strongly. In region 2, the membrane is selective for the strongly adsorbing molecule. In region 3, the molecules have significantly different diameters and adsorption strengths. The effects of each mechanism may combine to enhance separation or compete to reduce the selectivity.

Transport of gases through a crystalline molecular sieve membrane can also be influenced by any "nonzeolite pores" in the membrane structure. "Nonzeolite pores" are pores not formed by the crystal framework. Intercrystalline pores are an example of nonzeolite pores. The contribution of nonzeolite pores to the flux of gas through a zeolite-type membrane depends on the number, size and selectivity of these pores. If the nonzeolite pores are sufficiently large, transport through the membrane can occur through Knudsen diffusion or viscous flow. For MFI zeolite membranes, it has been reported that nonzeolite pores that allow viscous and Knudsen flow decrease the selectivity (Poshusta, J. C. et al., 1999, "Temperature and Pressure Effects on $CO_2$ and $CH_4$ permeation through MFI Zeolite membranes," J. Membr. Sci., 160, 115).

The modified membranes of the invention are selectively permeable to some gases over others. For example, the modified SAPO-34 membranes of the invention can be selectively permeable to $CO_2$ over $CH_4$. Therefore, the invention provides a method for separating two gases in a feedstream including these two gas components using the membranes of the invention. The feedstream is applied to the feed side of the membrane, generating a retentate stream and a permeate stream. In order to separate the two gases, sufficient transmembrane driving force must be applied that at least one of the gases permeates the membrane. In an embodiment, both gases permeate the membrane. If the membrane is selectively permeable to a first gas component over a second gas component, the permeate stream will be enriched in the first gas component while the retentate stream will be depleted in the first component. The permeate stream being enriched in the first gas component implies that the concentration of the first gas component in the permeate stream is greater than its concentration in the feedstream. Similarly, the retentate stream being depleted in the first gas component implies that the concentration of the first gas component in the retentate stream is less than its concentration in the feedstream.

The modified membranes of the invention are suitable for separating permanent gases, organic vapors, and combinations thereof.

Membrane Synthesis

Molecular sieve membranes may be grown through in-situ crystallization on a porous support to form a supported membrane. As used herein, a supported membrane is a membrane attached to a support. Gels for forming molecular sieve crystals are known to the art, but preferred gel compositions for forming membranes may differ from preferred compositions for forming loose crystals or granules. The preferred gel composition may vary depending upon the desired crystallization temperature and time.

In an embodiment, the molecular sieve membrane may be formed by providing a porous support, contacting the porous support with a molecular sieve-forming gel comprising an organic templating agent, heating the porous support and molecular sieve forming gel to form a zeolite layer at least in part on the surface of the porous support; and calcining the zeolite layer to remove the template. For some types of molecular sieves, it may be desirable to prepare the porous support by "seeding" it with molecular sieve crystals prior to contacting the support with the molecular sieve-forming gel. The term "templating agent" or "template" is a term of art and refers to a species added to the synthesis media to aid in and/or guide the polymerization and/or organization of the building blocks that form the crystal framework.

Synthesis mixtures for forming zeolite crystals are known to the art. Procedures for making A-type (Linde Type A) zeolite membranes on a porous substrates have been reported in the literature (Aoki, K. et al., "Gas Permeation Properties of A-Type Zeolite Membrane Formed on Porous Substrate by Hydrothermal Synthesis", 1998, 141, 197 and Masuda, T. et al., "Preparation of an A-Type Zeolite Film on the Surface of an Alumina Ceramic Filter", 1995, Microporous Mater., 3, 565).

MFI-type membranes include ZSM-5 and silicalite-1 membranes. As used herein, the term "silicalite-1" refers to zeolite Pentasil (silicalite-1; Si-rich ZSM-5) Procedures for making supported MFI-type membranes have been reported (Gues, E. R. et al., "Characterization of Zeolite (MFI) Membranes on Porous Ceramic Supports, 1992, J. Chem. Soc. Faraday Trans., 88, 3101; Yan. Y, et al. "Zeolite ZSM-5 Membranes Grown on Porous $\alpha$-$Al_2O_3$," 1995, JCS Chem. Commun., 2, 227; Masuda, T. at al., "Preparation of a Dense ZSM-5 Zeolite Film on the Outer of an Alumina Ceramic Filter," 1994, Appl. Catal. 111, 143; Bakker, W. J. et al., "Single and Multi-Component Transport Through Metal Supported MFI Zeolite Membranes," 1993, *Precision Process Technology*, M. P. C Weijnen and A. A. H. Drinkenburg, eds., Kluwer, Amsterdam, p. 425; Bakker, W. J. et al, "Permeation Characteristics of a Metal-Supported Silicalite-1 Zeolite Membrane," 1996, J. Membrane Sci., 117, 57). Jia et al. (1993) J. Membrane Sci. 82:15, discloses the synthesis of silicalite membranes on ceramic disks. B-ZSM-5, Fe-ZSM-5, Ga-ZSM-5 and Ge-ZSM-5 membranes are disclosed in U.S. Pat. No. 6,767,384 to Tuan An Vu et al. as well as by Tuan et al. (Tuan, V. A., et al., "Separating Organics from Water by Pervaporation with Isomorphously-Substituted MFI Zeolite Membranes", 2002 J. Membrane Science 196, 111-123).

MEL membranes include ZSM-11. Procedures for making ZSM-11 membranes have been reported by Li et al. (Li, S., et al., 2002, "ZSM-11 Membranes: Characterization and Pervaporation Performance for Alcohol/Water Mixtures," AlChE Journal 48, 269-278).

Procedures for making DD3R membranes on a porous support have been reported by Tomita et al. (T. Tomita, K. Nakayama, H. Sakai, 2004, "Gas separation characteristics of DDR type zeolite membrane," *Micropor. Mesopor. Mater.* 68, 71).

SAPO crystals can be synthesized by hydrothermal crystallization from a reaction mixture containing reactive sources of silica, alumina, and phosphate, and an organic templating agent. Lok et al. (U.S. Pat. No. 4,440,871) report gel compositions and procedures for forming several types of SAPO crystals, including SAPO-5, SAPO-11, SAPO-16, SAPO-17, SAPO-20, SAPO-31, SAPO-34, SAPO-35, SAPO-37, SAPO-40, SAPO 41, SAPO-42, and SAPO-44 crystals. Lok et al. do not appear to disclose formation of SAPO membranes. Mériaudeu et al. (Mériaudeau, P. et al., J. Catalysis, 1997, 169, 55-66) report gel compositions and procedures for forming SAPO-11, SAPO-31, and SAPO-41 crystals. Mériaudeu et al. do not appear to disclose formation of SAPO membranes. Prakash and Unnikrishnan report gel compositions and procedures for forming SAPO-34 crystals. (Prakash, A. M. and Unnikrishnan, S., J. Chem. Sc. Faraday Trans., 1994, 90(15), 2291-2296). In several of Prakash and Unnikrishnan's reported procedures, the gel was aged for 24 hours at 27° C. (300 K). Prakash and Unnikrishnan do not appear to disclose formation of SAPO-34 membranes.

In an embodiment for forming SAPO membranes, the gel is prepared by mixing sources of aluminum, phosphorus, silicon, and oxygen in the presence of a templating agent and water. The composition of the mixture may be expressed in terms of the following molar ratios as: $1.0\ Al_2O_3$:$aP_2O_5$:$bSiO_2$:$cR$:$dH_2O$, where R is a templating agent. In an embodiment, R is a quaternary ammonium templating agent. In an embodiment, the quaternary ammonium templating agent is selected from the group consisting of tetrapropyl ammonium hydroxide (TPAOH), tetrapropyl ammonium bromide, tetrabutyl ammonium hydroxide, tetrabutyl ammonium bromide, tetraethyl ammonium hydroxide (TEAOH), tetraethyl ammonium bromide, or combinations thereof. In an embodiment, suitable for crystallization between about 420 K and about 500 K, a is between about 0.01 and about 52, b is between about 0.03 and about 196, c is between about 0.2 and about 5 and d is between about 20 and about 300. If other elements are to be substituted into the structural framework of the SAPO, the gel composition can also include $Li_2O$, BeO, MgO, CoO, FeO, MnO, ZnO, $B_2O_3$, $Ga_2O_3$, $Fe_2O_3$, GeO, TiO, $As_2O_5$ or combinations thereof.

In an embodiment suitable for crystallization of SAPO-34, c is less than about 2. In an embodiment suitable for crystallization of SAPO-34 at about 473K for about 20 hours, a is about 1, b is about 0.6, c is about 1.07 and d is about 56. In an embodiment, R is a quaternary organic ammonium templating agent selected from the group consisting of tetrapropyl ammonium hydroxide, tetraethyl ammonium hydroxide (TEAOH), or combinations thereof. Examples of procedures for making SAPO-34 membranes on porous supports have been reported in the scientific literature. Lixiong et al. (Stud. Surf. Sci. Catl., 1997, 105, p 2211) reported synthesis of a SAPO-34 membrane on one side of a porous $\alpha$-$Al_2O_3$ disk by immersing the substrate surface in a hydrogel and heating the substrate and gel. Lixiong et al. reported single gas permeances for $H_2$, $N_2$, $CO_2$, and $n$-$C_4H_{10}$. Poshusta et al. (Ind. Eng. Chem. Res., 1998, 37, 3924-3929; AlChE Journal, 2000, 46(4), 779-789) reported hydrothermal synthesis of SAPO-34 membranes on the inside surface of asymmetric, porous $\alpha$-$Al_2O_3$ tubes. Poshusta et al. (supra) reported single gas and mixture permeances and ideal and mixture selectivities for several gases, including $CO_2$ and $CH_4$. The $CO_2$/$CH_4$ selectivities reported for a 50/50 $CO_2$/$CH_4$ mixture at 300K were between 14 and 36 for a feed pressure of 270 kPa and a pressure drop of 138 kPa (Poshusta et al., AlChE Journal, 2000, 46(4), pp 779-789). The $CO_2$/$CH_4$ selectivity was attributed to both competitive absorption (at lower temperatures) and differences in diffusivity.

In an embodiment suitable for crystallization of SAPO-5 at about 460 K for about 24 hours, a is about 1.0, b is about 0.4, c is about 2.0. and d is about 50. In an embodiment, R is a tripropylamine template (Gump, C. et al., 2001, Ind. Engr. Chem. Res, 40(2), 565-577). In an embodiment suitable for crystallization of SAPO-11 at about 460K for about 24 hours, a is about 1.0, b is about 0.4, c is about 1.5, and d is about 50. In an embodiment, R is a dipropylamine template (Gump, C. et al., 2001, Ind. Engr. Chem. Res, 40(2), 565-577). Procedures for making SAPO-5 and SAPO-11 membranes have been reported in the scientific literature. Sano et al. (Sano, T. et al., 1992, J. Mol. Cat., 77, L12) reported hydrothermal synthesis of SAPO-5 membranes on a Teflon slab. Sano et al. reported aging of the hydrogel overnight at room temperature before heating the substrate and gel. Tsai et al. (Tsai, T. G. et al., 1998, Micropor. Mesopor. Mat., 22, 333) reported synthesis of SAPO-5 membranes on anodic alumina supports using a microwave hydrothermal synthesis technique. Gump et al. (Gump, C. et al., 2001, Ind. Engr. Chem. Res., 40(2), 565-577) reported hydrothermal synthesis of SAPO-5 and SAPO-11 membranes on the inner surface of $\alpha$-alumina tubes with 200 nm pores. In an embodiment for forming SAPO membranes, the gel is prepared by mixing sources of phosphate and alumina with water for several hours before adding the template. The mixture is then stirred before adding the source of silica.

In an embodiment, the source of phosphate is phosphoric acid. Suitable phosphate sources also include organic phosphates such as triethyl phosphate, and crystalline or amorphous aluminophosphates. In an embodiment, the source of alumina is an aluminum alkoxide, such as aluminum isopropoxide. Suitable alumina sources also include pseudoboehmite and crystalline or amorphous aluminophosphates (gibbsite, sodium aluminate, aluminum trichloride). In an embodiment, the source of silica is a silica sol. Suitable silica sources also include fumed silica, reactive solid amorphous precipitated silica, silica gel, alkoxides of silicon (silicic acid or alkali metal silicate).

The molecular sieve-forming gel may be aged prior to use. As used herein, an "aged" gel is a gel that is held (not used) for a specific period of time after all the components of the gel are mixed together. In an embodiment, the gel is sealed and stirred during storage to prevent settling and the formation of a solid cake. Without wishing to be bound by any particular theory, it is believed that aging of the gel affects subsequent crystallization of the gel by generating nucleation sites. In general, it is believed that longer aging times lead to formation of more nucleation sites. The preferred aging time will depend upon the aging temperature selected. Preferably, crystal precipitation is not observed during the aging period. Preferably, the viscosity of the aged gel is such that the gel is capable of penetrating the pores of the porous support. After initial mixing of the components of the synthesis gel in a container, material can settle to the bottom of the container. In an embodiment, the gel is stirred and aged until no settled material is visible at the bottom of the container and the gel appears translucent and substantially uniform to the eye. In different embodiments, the aging time at room temperature for SAPO-forming gels is at least about twenty-four hours, greater than about twenty-four hours, at least about forty-eight hours, and at least about seventy-two hours. For SAPO-34 membranes, in different embodiments the aging time at room temperature can be at least about forty-eight hours, at least about seventy-two hours, and between about three days and about seven days. The same batch of gel may be used for all the crystallization steps, so long as the upper limit of the aging time is not exceeded. Alternately, more than one batch of gel may be prepared and aged, with different batches being used for one or more crystallization step(s). In an embodiment, each crystallization step may use a different batch of gel. The aging time of different batches of gel at the time of use may be the same or may be different.

The gel is brought into contact with at least one surface of the porous support. In an embodiment, the porous support may be immersed in the gel so that more than one surface of the porous support contacts the gel. In an embodiment, at least some of the gel penetrates the pores of the support. The pores of the support need not be completely filled with gel. In an embodiment, the porous support is brought into contact with a sufficient quantity of gel such that growth of the molecular sieve membrane is not substantially limited by the amount of gel available.

The porous support is a body capable of supporting the molecular sieve membrane. The porous support may be of any suitable shape, including disks and tubes. In an embodiment, the porous support is in the form of a tube. In an embodiment, the porous support is a metal or an inorganic material. In an embodiment, the porous support does not appreciably dissolve or form reaction products at the interface when placed in contact with the synthesis gel. Suitable inorganic porous supports include, but are not limited to, α-alumina, glass, titania, zirconia, carbon, silicon carbide, clays or silicate minerals, aerogels, supported aerogels, and supported silica, titania and zirconia. Suitable porous metal supports include, but are not limited to, stainless steel, nickel based alloys (Inconel, Hastalloy), Fecralloy, chromium and titanium. The metal may be in the form of a fibrous mesh (woven or non-woven), a combination of fibrous metal with sintered metal particles, and sintered metal particles. In an embodiment, the metal support is formed of sintered metal particles. The pore diameter of the support is preferably large enough to allow the synthesis gel to penetrate the support. Furthermore, the pore diameter of the support is preferably large enough so that molecular sieve crystals can form inside the support. Often, a porous support will have a distribution of pore sizes. Preferably, the pore diameter of the support is greater than about 0.2 microns. The pore diameter of the support being greater than about 0.2 microns does not require that every single pore in the support is greater than about 0.2 microns, but it does exclude supports having regions where the characteristic pore size is about 0.2 microns (for example, a support having a layer with an 0.2 micron average pore size). The characteristic pore size may be taken as the average, median or largest pore size. In different embodiments, the pore size of the support is greater than about 1 micron, between about 2 and about 6 microns, or about 4 microns. The porous support may be joined to nonporous material which provides a sealing surface for use of the membrane. This nonporous material may also be immersed in or partially covered with synthesis gel during the synthesis process, in which case molecular sieve crystals may form on the nonporous material as well.

In an embodiment, the porous support is cleaned prior to being brought into contact with the synthesis gel. The support may be cleaned by being boiled in purified water. After cleaning with water, the support may then be dried.

After the porous support and the aged gel are brought into contact, the support and gel are heated in a molecular sieve crystal synthesis step. This synthesis step can lead to formation of molecular sieve crystals on and in the porous support. During each synthesis step a layer of molecular sieve crystals can be said to form on the surface of the porous support and/or on previously formed molecular sieve crystals. The layer of molecular sieve crystals formed during each synthesis step may not be continuous. During the synthesis step, crystals may also precipitate from the synthesis gel without being incorporated into the molecular sieve membrane. In an embodiment for synthesis of SAPO-34 membranes, the synthesis temperature is between about 420K and about 500K. In different embodiments for synthesis of SAPO-34 membranes, the synthesis temperature is between about 450 K and about 480 K, or between about 465K and about 480 K. In different embodiments, the crystallization time for SAPO-34 membranes is between about 15 and about 25 hours, or about 20 hours. Synthesis typically occurs under autogenous pressure.

In an embodiment, excess synthesis gel is removed from the support and the molecular sieve crystals after each synthesis step. The excess gel may be removed by washing with water. After washing with water, the support and molecular sieve crystals may then be dried.

In an embodiment, the synthesis step may be repeated in order to form a greater amount of molecular sieve crystals. After each synthesis step, the excess synthesis gel is removed and then the porous support is brought into contact with synthesis gel before performing the next synthesis step. In an embodiment, sufficient synthesis steps are performed so that the cumulative layer formed on the support surface by the synthesis steps forms a continuous layer. The molecular sieve membrane is formed by the cumulative layer(s) of molecular sieve crystals formed on the support surface(s) and the (interconnected) molecular sieve crystals formed inside the porous support. In an embodiment, the molecular sieve crystals inside the support are substantially interconnected. In an embodiment, the interconnected molecular sieve crystals are connected to the layers of molecular sieve crystals formed on the support surface. In an embodiment, sufficient synthesis steps are performed that the membrane is impermeable to nitrogen after preparation (but before calcination).

After molecular sieve crystal synthesis is complete, the molecular sieve membranes are calcined to substantially remove the organic template material. After calcination, the membrane becomes a semi-permeable barrier between two phases that is capable of restricting the movement of molecules across it in a very specific manner. In different embodiments, the calcination temperature for SAPO membranes is between about 600 K and about 900K, and between about 623 K and about 773 K. For SAPO membranes made using TEOH and TPAOH as a templating agent, the calcining temperature can be between about 623 K and about 673 K. In an embodiment, the calcination time is between about 15 hours and about 25 hours. Longer times may be required at lower temperatures in order to substantially remove the template material. Use of lower calcining temperatures can reduce the formation of calcining-related defects in the membrane. The heating rate during calcination should be slow enough to limit formation of defects such as cracks. In an embodiment, the heating rate is less than about 2.0 K/min. In a different embodiment, the heating rate is about 0.6 K/min. Similarly, the cooling rate must be sufficiently slow to limit membrane defect formation. In an embodiment, the cooling rate is less than about 2.0 K/min. In a different embodiment, the cooling rate is about 0.9 K/min.

In an embodiment, the molecular sieve membranes of the present invention comprise molecular sieve crystals which are present within at least some of the pores of the support and which form a layer on at least one side of the porous support. The thickness of the molecular sieve layer depends in part on the number of synthesis steps performed. In an embodiment where synthesis steps are performed until the membrane is impermeable to nitrogen, the thickness of the cumulative molecular sieve layer is less than about 20 microns. When the layer thicknesses are measured from cross-sections with scanning electron microscopy, the uncertainty in the thickness measurement is believed to be on the order of ±10%. In another embodiment, the thickness of the molecular sieve layer is about 5 microns. In an embodiment, immersion of a porous support in the synthesis gel can lead to formation of molecular sieve crystals within the support as well as on both sides of the support. For example, immersion of a porous tube in the synthesis gel can lead to formation of molecular sieve crystals within the tube as well as formation of a molecular sieve layer on the inside and the outside of the tube. In an embodiment, the molecular sieve crystals may form throughout the thickness of the support. When both sides of the support are immersed and capable of being penetrated by the gel, formation of molecular sieve crystals throughout the thickness of the support indicates that the synthesis gel has penetrated to the center of the support. However, formation of molecular sieve crystals throughout the support does not require that molecular sieve crystals completely fill the pore space of the support.

In an embodiment, $CO_2/CH_4$ separation selectivity of the SAPO-34 membranes of the invention before modification is at least 50. In an embodiment, the $CO_2/CH_4$ separation selectivity of the SAPO-34 membranes of the invention before modification is greater than about 200 at a temperature of about 253 K for an approximately 50/50 $CO_2/CH_4$ mixture with about 3 MPa pressure drop. In an embodiment, the $CO_2/CH_4$ separation selectivities of the SAPO-34 membranes of the invention are greater than about 140 at a temperature of about 253 K with about 3 MPa pressure drop for $CO_2/CH_4$ mixtures with $CO_2$ concentration varying from approximately 25 to approximately 70%.

Membrane Modification

The calcined molecular sieve membrane is treated with a modifying agent. The modifying agent is a compound, which, when adsorbed, is capable of improving the separation selectivity of the membrane. In different embodiments, the modifying agent is adsorbed within the membrane, on the membrane, or both within and on the membrane. In an embodiment, $CO_2/CH_4$ separation selectivity is improved. In an embodiment, the methane flux through the membrane is below readily detectable levels. In other embodiments, the improvement in the separation selectivity is at least one order of magnitude, at least two orders of magnitude, or at least three orders of magnitude.

The combination of molecular sieve and modifying agent can be "tuned" for a given separation. For tuning the molecular sieve and modifying agent, key issues include the size and shape of the modifying agent as well as its affinity for the molecular sieve (sorption strength). In an embodiment, the modifying agent is ammonia. Other potentially useful modifying agents include silanes and/or amines that react with the acid sites of zeolites and polar compounds such as ethanol.

Adsorption of the modifying agent within the membrane may be through chemisorption, physisorption, or a combination thereof. The process of chemisorption according to the present invention is a chemical adsorption process in which a weak chemical bond is formed between molecules in the gaseous or liquid state (the modifying agent) and a solid surface (the molecular sieve). Due to this weak bonding the process is reversible upon the application of heat. In the case of physisorption the modifying agent may be adsorbed on to the surface by relatively weak forces such as van der Waals forces. In the practice of the invention, the modifying agent does not irreversibly react with the molecular sieve.

Adsorption may occur within the "zeolite" pores, the "non-zeolite" pores, or combinations thereof. Without wishing to be bound by any particular belief, adsorption of the modifying agent within the membrane may serve to obstruct gas flow through "non-zeolite" membrane pores, therefore improving the membrane selectivity.

In an embodiment, the modifying agent is ammonia. In this embodiment, the treated membrane may be said to be ammoniated. When the molecular sieve membrane is in acid form and contains Brønsted acid sites (acid sites where the acidic entity is an ionizable hydrogen), ammoniation of the membrane may lead to the formation of ammonium ions at these acid sites. It is believed that the ammonia treatment used in the invention does not result in nitridation of the molecular sieve.

In an embodiment, the modifying agent is not a nitrogen containing compound selected from the group consisting of amines, monocyclic heterocyclic compounds, organonitrile compounds and mixtures thereof. In another embodiment, the modifying agent is not a polynuclear aromatic heterocyclic compound.

In an embodiment, the membrane may be modified by flowing a gas comprising the modifying agent through the membrane. The gas may further comprise a diluent such as nitrogen. In another embodiment, the membrane may be modified in solution.

The use temperature of the modified membrane may be influenced by conditions at which the modifying agent begins to desorb from the membrane. For strongly ammoniated SAPO-34 crystals modified with ammonia, purged in a flow of dry nitrogen, some desorption of ammonia was observed at 295K, while greater effects were seen at 413 K ((Buchholz et al., 2004, J. Phys. Chemistry, Vol. 108, pp 3107-3113).

Every formulation or combination of components described or exemplified can be used to practice the invention, unless otherwise stated. Specific names of compounds are intended to be exemplary, as it is known that one of ordinary skill in the art can name the same compounds differently. When a compound is described herein such that a particular isomer or enantiomer of the compound is not specified, for example, in a formula or in a chemical name, that description is intended to include each isomer and enantiomer of the compound described individual or in any combination. When a Markush group or other grouping is used herein, all individual members of the group and all combinations and subcombinations possible of the group are intended to be individually included in the disclosure.

Whenever a range is given in the specification, for example, a temperature range, a time range, or a composition range, all intermediate ranges and subranges, as well as all individual values included in the ranges given are intended to be included in the disclosure.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements. The invention illustratively described herein suitably may be practiced in the absence of any element or elements, limitation or limitations which is not specifically disclosed herein.

The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. One of ordinary skill in the art will appreciate that methods, device elements, starting materials, and synthetic methods other than those specifically exemplified can be employed in the practice of the invention without resort to undue experimentation. All art-known functional equivalents, of any such methods, device elements, starting materials, and synthetic methods are intended to be included in this invention.

Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

All patents and publications mentioned in the specification are indicative of the levels of skill of those skilled in the art to which the invention pertains.

All references cited herein are hereby incorporated by reference to the extent that there is no inconsistency with the disclosure of this specification. Some references provided herein are incorporated by reference herein to provide details concerning additional starting materials, additional methods of synthesis, additional methods of analysis and additional uses of the invention.

Example 1

Preparation of SAPO-34 Membranes

SAPO-34 membranes were prepared on porous stainless steel tubes. These tubes had approximately 4-μm pores, a length of approximately 30 mm, an inner diameter of approximately 7.2 mm and an outer diameter of approximately 9.5 mm (81180-017-PRDC-TEST, Pall Corporation). Non-porous, stainless steel tubes were welded onto each end of the stainless steel support to prevent membrane bypass and to provide a sealing surface for o-rings. The combined length of the combined porous and dense tube assembly was approximately 59 mm. The permeate area was approximately 7.8 cm$^2$. Before synthesis, the tube assembly was boiled in purified water for 3 h and dried at 373 K under vacuum for 30 min.

The synthesis gel had the approximate molar composition: $Al_2O_3:P_2O_5:0.6$ $SiO_2:1.07$ TEAOH:56 $H_2O$, and was prepared by stirring $H_3PO_4$ (85 wt % aqueous solution), Al(i-$C_3H_7O)_3$ (>99.99%, Aldrich), and $H_2O$ at room temperature for 12 h. Then the template, tetra-ethyl ammonium hydroxide (TEAOH, 35 wt % aqueous solution, Aldrich), was added, and the mixture was stirred for 30 min before the colloidal silica sol (Ludox AS40, 40% aqueous solution) was added. The solution was sealed and stirred during storage to prevent settling and the formation of a solid cake. The gel was aged for approximately 3 days at room temperature before use.

For membranes forming a layer primarily on the inside surface of the tube, the outside of the stainless steel tube was wrapped with Teflon tape before synthesis. The stainless tube assembly was directly placed vertically in a Teflon tube in an autoclave. The Teflon tube was then filled with synthesis gel to cover the end of the stainless tube assembly. Typically, the gel level was approximately 10 mm above the upper end of the stainless tube assembly. An approximately 24.5 mm diameter and approximately 104 mm high Teflon tube holds approximately 35 ml of synthesis gel and three stainless tube assemblies. An approximately 41 mm diameter and approximately 100 mm high Teflon tube holds approximately 50 ml of synthesis gel and eight stainless tube assemblies. The hydrothermal synthesis was carried at about 473 K for about 20 h. After synthesis, the membrane was washed with purified water at 297 K and dried at about 373 K in an oven for about 10 mins. A second synthesis layer was applied using the same procedure, but the tube was inverted to obtain a more uniform layer. The third and fourth synthesis layers (if used) were prepared using the same procedure as the first and second layers, except that a new batch of aged synthesis gel was used. Good quality membranes were prepared with 3-4 synthesis.

Membranes were impermeable to $N_2$ after preparation but before calcination. To remove the TEAOH template from the zeolite framework, membranes were calcined at about 663 K for about 20 h. The heating and cooling rates were about 0.6 and about 0.9 K/min, respectively.

Figure 1B:
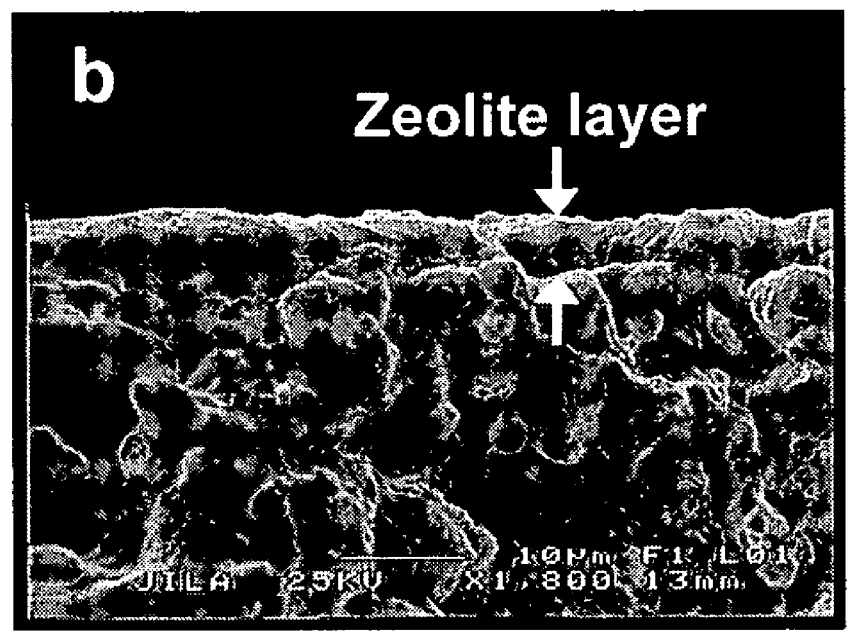

FIGS. 1A and 1B show SEM photos of a SAPO-34 membrane prior to modification. FIG. 1A shows the surface, while FIG. 1B shows a cross sectional view.

Example 2

Modification of SAPO-34 Membranes

Membranes made on the inside of a tube as described in Example 1 were mounted in a stainless steel module, and sealed at each end with silicone O-rings. The module was heated to 220° C., and $NH_3$ gas was then introduced to the membrane for 2 h. The feed pressure was 118 kPa and the permeate pressure was 84 kPa. Without wishing to be bound by any particular belief, it is believed that that the $NH_3$ reacted with the acid sites of the SAPO-34 to form $NH_4^+$-SAPO-34.

Example 3

Transport Properties of SAPO-34 Membranes

Single-gas and mixture permeation was measured on a system similar to that used by Poshusta et al. (Ind. Eng. Chem. Res., 1998, 37. p. 3924), but modified for the study of light gases at pressure drop as high as 3 MPa. The membranes were mounted in a stainless-steel module, and sealed at each end with silicone O-rings. Fluxes were measured using a soap-film bubble flowmeter and a stopwatch. The lowest measurable permeance was estimated to be $9.6 \times 10^{-11}$ mol/($m^2$ s Pa).

Carbon dioxide and $CH_4$ single gas and mixture permeation was investigated as a function of temperature and pressure drop for some membranes. For mixture separation, mass flow controllers were used to mix pure $CO_2$ and $CH_4$ gases. The total flow rate was 1300 mL/min for most of the experiments. The pressure on each side of the membrane was independently controlled between 84 kPa and 3.4 MPa. To carry out gas separation below room temperature, the membrane module and some system lines were placed into an ethyl glycol/water (50/50) bath. The lowest temperature investigated was about 250 K. The compositions of the feed, retentate, and permeate streams were measured using a Hewlett-Packard 5890/series II gas chromatograph equipped with a thermal conductivity detector and HAYESEP-D column (Altech). The oven, injector, and detector temperatures were all kept at 423 K.

Unless otherwise noted, the experimental results shown are for SAPO-34 membranes forming a layer primarily on the inside surface of the support as described in Example 1 and treated with ammonia as described in Example 2. Gas concentrations are molar concentrations.

Single Gas Measurements

Figure 2:
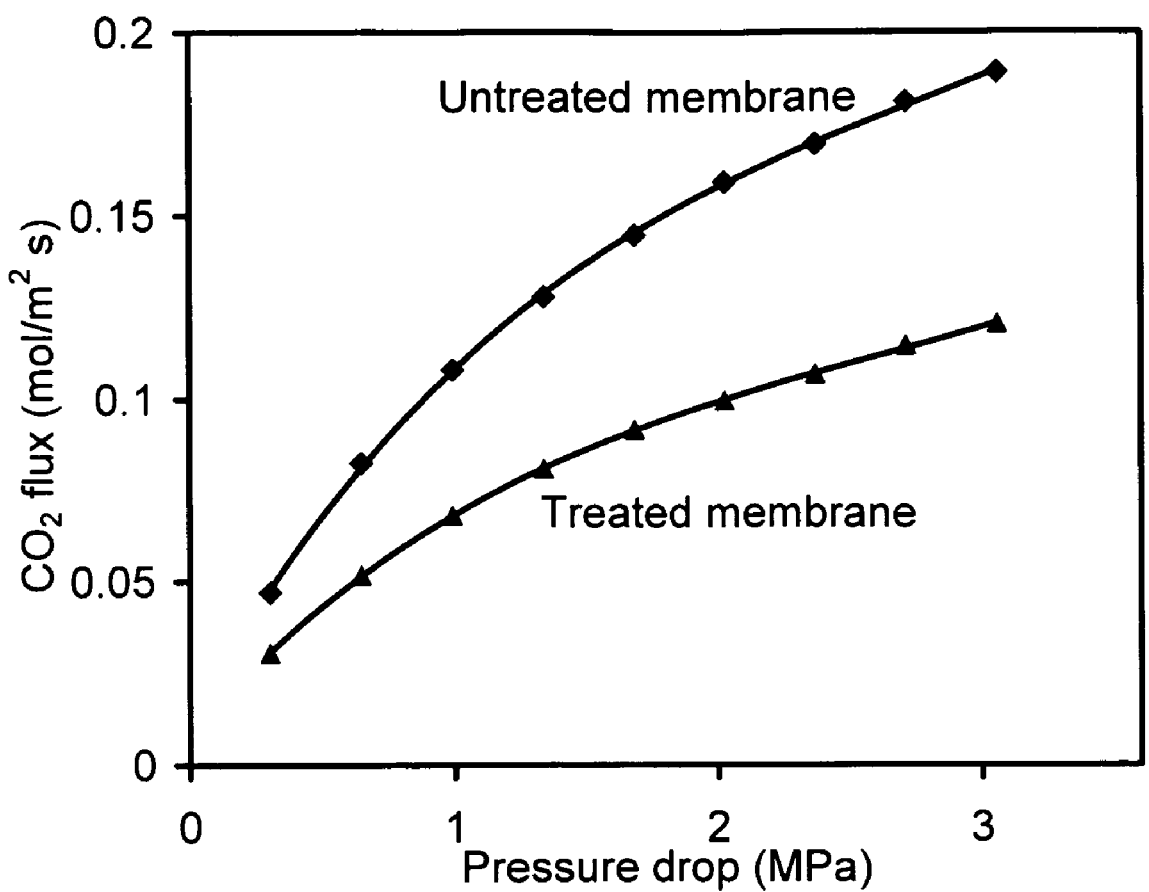
FIG. 2 shows gas single fluxes for $CO_2$ at 295 K through an untreated and a $NH_3$ treated SAPO-34 membrane as a function of pressure drop. The permeate pressure was 0.08 MPa.
Figure 3:
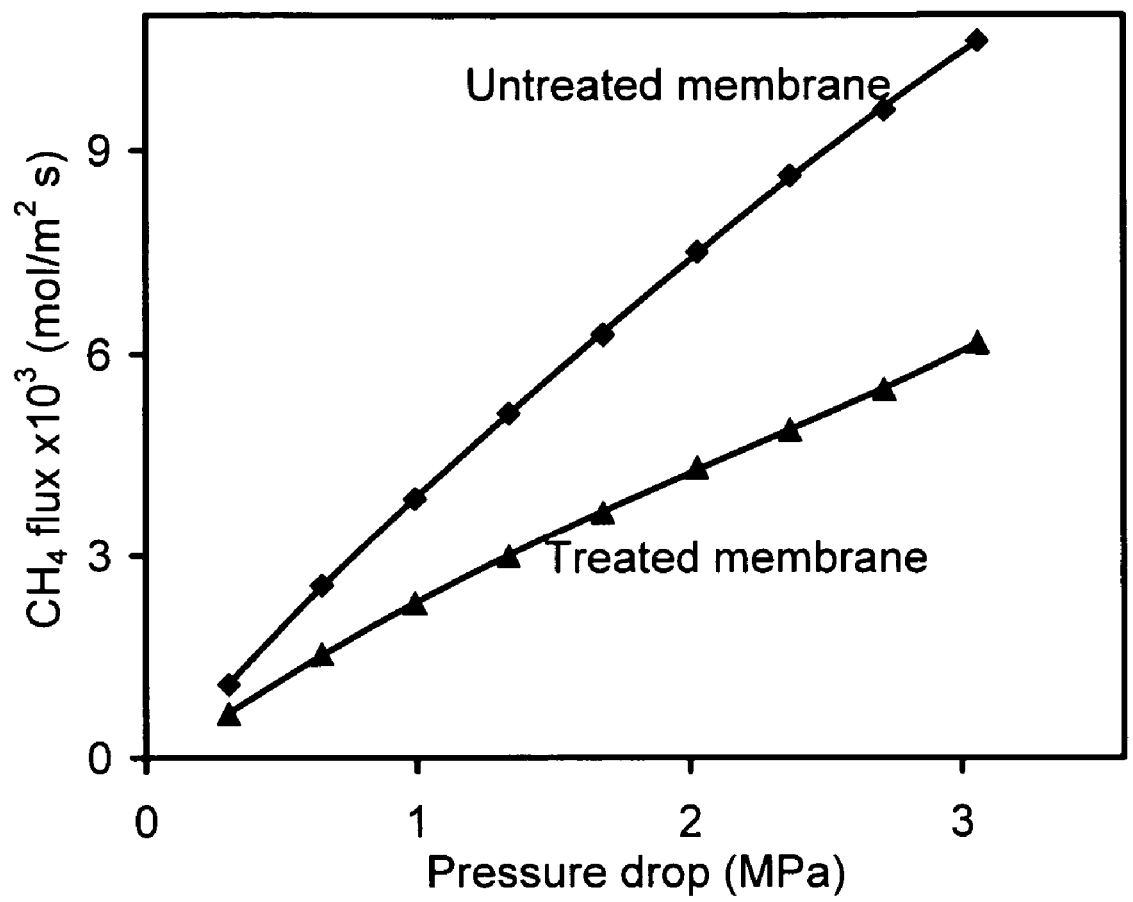
FIG. 3 shows single gas fluxes for $CH_4$ at 295 K through an untreated and a $NH_3$ treated SAPO-34 membrane as a function of pressure drop. The permeate pressure was 0.08 MPa.
Figure 4:
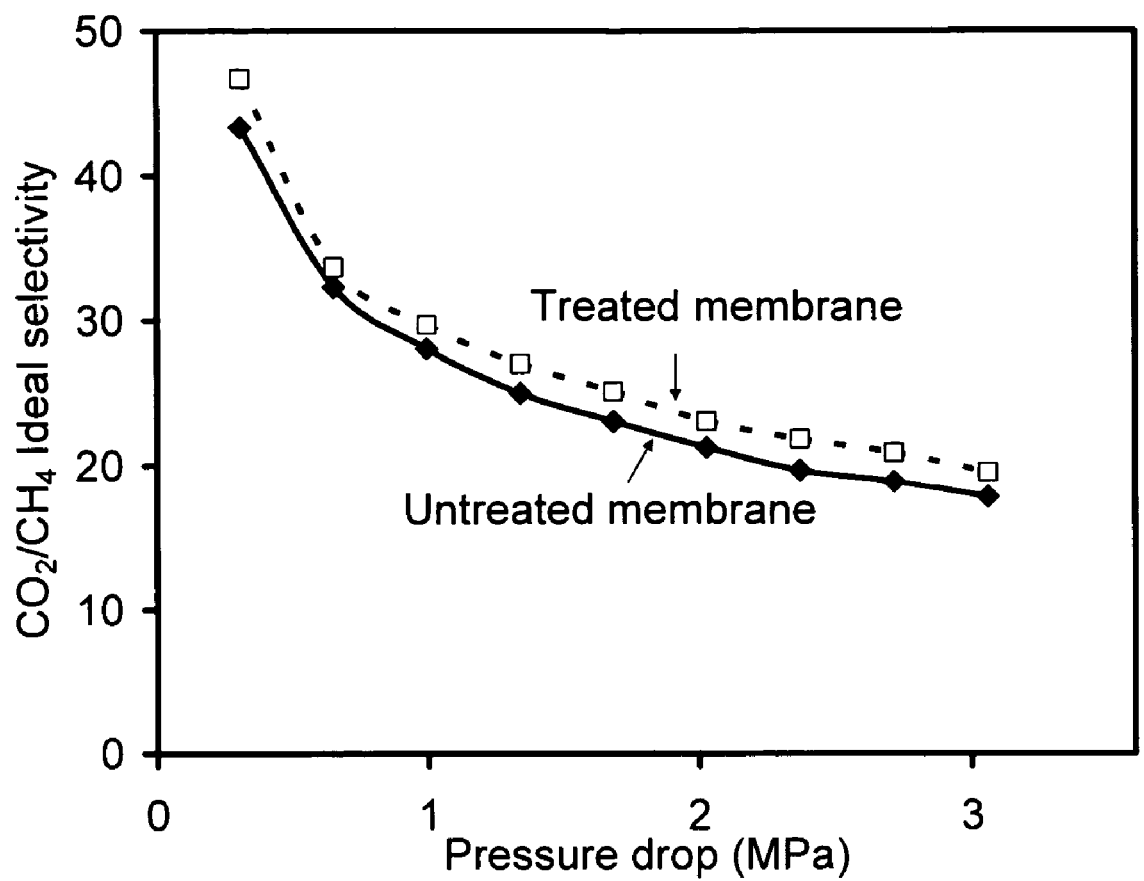
FIG. 4 shows $CO_2/CH_4$ ideal selectivity at 295 K through an untreated and a $NH_3$ treated SAPO-34 membrane as a function of pressure drop. The permeate pressure was 0.08 MPa.

FIGS. 2-4 show single gas fluxes for $CO_2$ and $CH_4$, and $CO_2/CH_4$ ideal selectivities as a function of pressure drop through a SAPO-34 membrane before and after the $NH_3$ treatment. In FIGS. 2-4, the data markers for the untreated membranes are diamond-shaped. After ammonia treatment, the $CO_2$ permeance decreased by approximately 35% at approximately 0.3 kPa pressure drop and approximately 36% at approximately 3 MPa pressure drop. Similarly, the $CH_4$ permeance decreased by 40-42% as compared to the unmodified membrane as pressure drop increased from 0.3 to 3.0 MPa. The $CO_2/CH_4$ ideal selectivity slightly increased after the $NH_3$ treatment, as shown in FIG. 4

Figure 5:
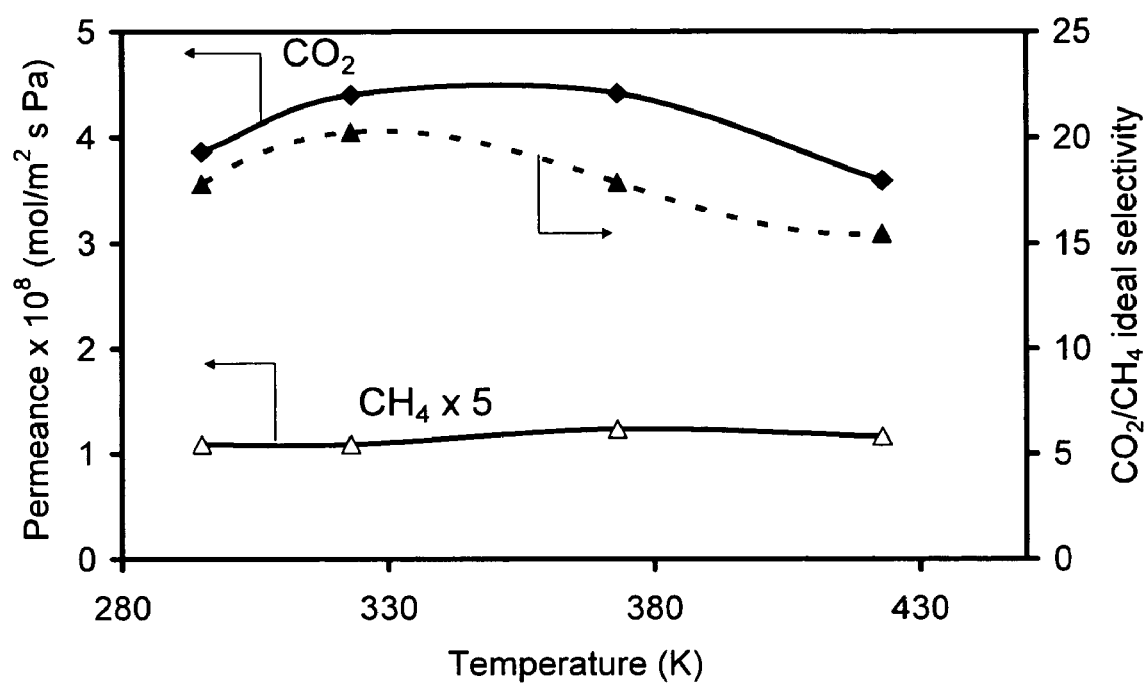
FIG. 5 shows single gas permeances for $CO_2$ and $CH_4$, and $CO_2/CH_4$ ideal selectivity through a $NH_3$ treated SAPO-34 membrane as a function of temperature. The feed pressure was 3.1 MPa and the permeate pressure was 0.08 MPa.

FIG. 5 shows single gas permeances for $CO_2$ and $CH_4$, and $CO_2/CH_4$ ideal selectivity as a function of temperature through a $NH_3$ treated SAPO-34 membrane. The feed pressure was 3.1 MPa and the permeate pressure was 0.08 MPa. As shown in FIG. 5, the $NH_3$ treated membrane shows a slight maximum in $CO_2$ permeance at about 323 K, whereas $CH_4$ permeance exhibited maximum at around 373 K. The highest $CO_2/CH_4$ ideal selectivity was 20, obtained at 323 K.

Gas Mixture Measurements

Figure 6:
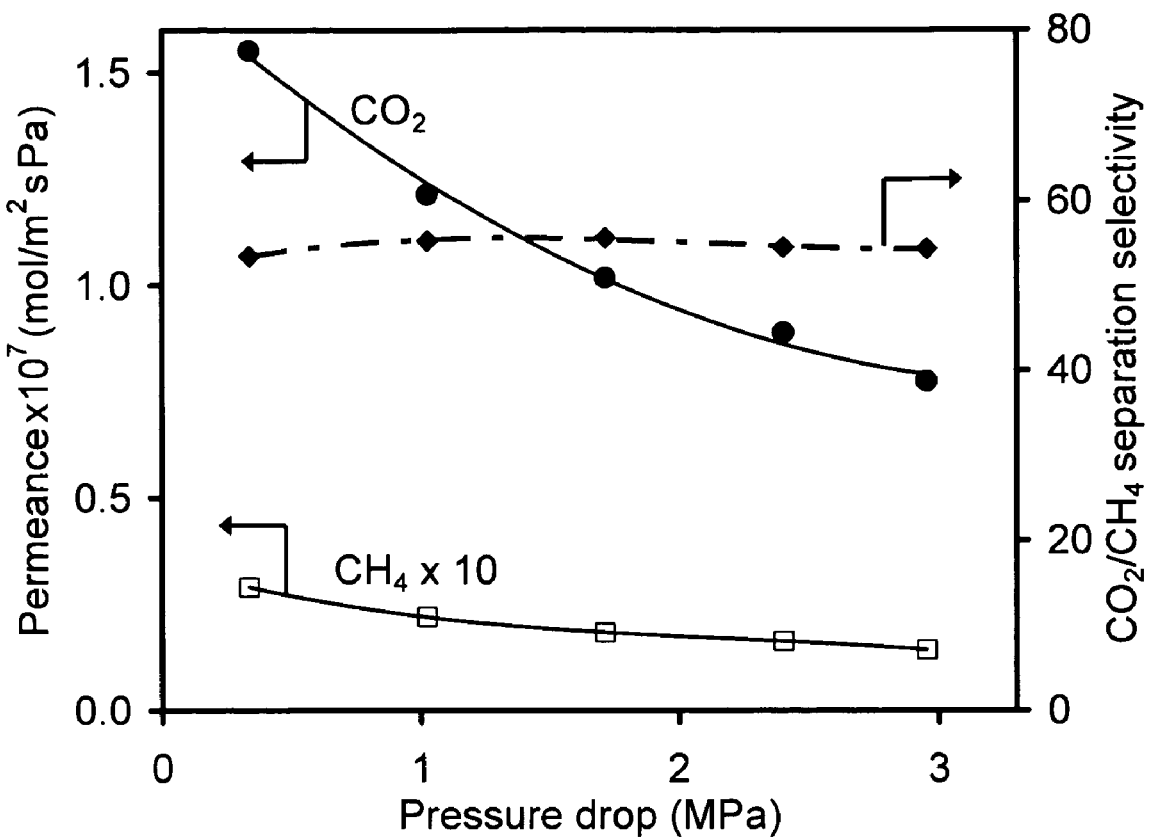
FIG. 6 shows the permeances for $CO_2$ and $CH_4$, and $CO_2/CH_4$ separation selectivity of a $CO_2/CH_4$ mixture (50/50) as a function of pressure drop for a SAPO-34 membrane prior to modification. The permeate pressure was 84 kPa and the temperature was 295 K.
Figure 7:
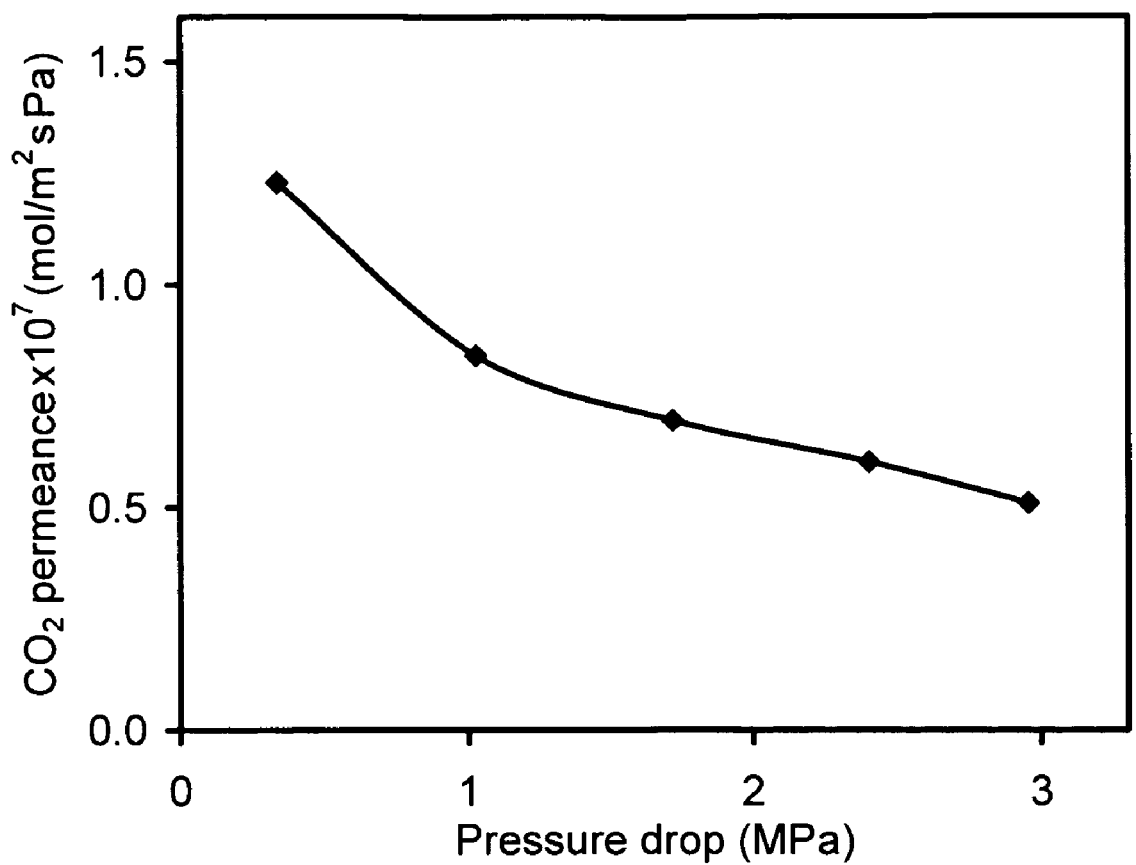
FIG. 7 shows the $CO_2$ permeance of a $CO_2/CH_4$ mixture (50/50) as a function of pressure drop for a $NH_3$ modified SAPO-34 membrane. The permeate pressure was 84 kPa and the temperature was 295 K.

FIG. 6 shows the permeances for $CO_2$ and $CH_4$, and $CO_2/CH_4$ separation selectivity of a $CO_2/CH_4$ mixture (50/50) as a function of pressure drop for a SAPO-34 membrane prior to modification. The permeate pressure was 84 kPa and the temperature was 295 K. The separation selectivity slightly increased as pressure drop increased because the fraction of permeance decreased more for $CH_4$ than $CO_2$ (FIG. 6). After modification, as shown in FIG. 7, the $CO_2$ permeance decreased by 21% at a pressure of 0.34 MPa and 34% at the pressure drop of 3.0 MPa. FIG. 7 shows that the ammonia treated SAPO-34 membrane still had a $CO_2$ permeance as high as $1.2 \times 10^{-7}$ mol/($m^2$ s Pa) at 295 K under a pressure drop of 0.34 kPa for a 50/50 $CO_2/CH_4$ gas mixture. The $CH_4$ permeate concentration was below the detection limit, which was estimated to be 36 ppm. Thus the $CO_2/CH_4$ separation selectivity was at least 42,000. This is an increase of about 3 orders of magnitude over SAPO-34 membranes that were not modified.

Figure 8:
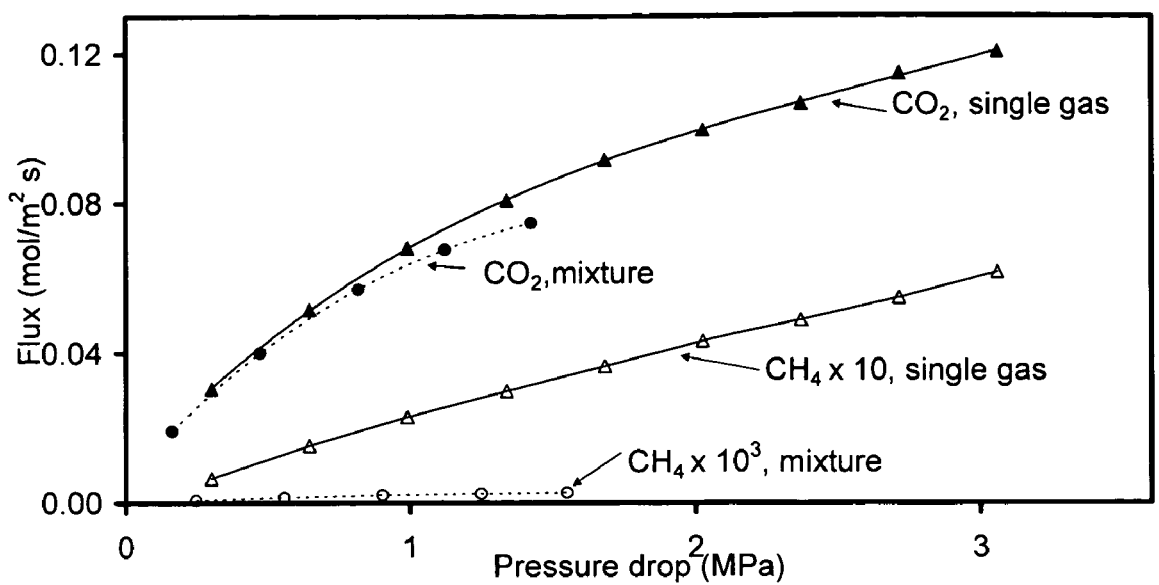
FIG. 8 is a comparison of $CO_2$ and $CH_4$ fluxes for single gases and a $CO_2/CH_4$ mixture (50/50) at 295 K as a function of partial pressure drop for a $NH_3$ treated SAPO-34 membrane.

FIG. 8 compares $CO_2$ and $CH_4$ fluxes for single gases and a $CO_2/CH_4$ mixture (50/50) at 295 K as a function of partial pressure drop for a $NH_3$ treated SAPO-34 membrane. The partial pressure drop was used for the mixture, and thus the mixture pressure drop is only to 1.5 MPa. The $CO_2$ flux was a little lower in the mixture, and this is the behavior predicted by the Maxwell-Stefan model. The model indicates that the slower-diffusing $CH_4$ slows the faster diffusing $CO_2$, even though the $CH_4$ flux is small. The $CH_4$ mixture fluxes were significantly lower than the single gas fluxes (FIG. 8). This lower $CH_4$ coverage in the mixture, relative to the single gas, may be due to competitive adsorption because $CO_2$ has a higher heat of adsorption than $CH_4$.

Table 1 illustrates the effect of temperature on $CO_2/CH_4$ separation at a feed pressure of 3.1 MPa for an $NH_3$-treated SAPO-34 membrane. For both temperatures tested, the $CH_4$ permeate concentration was still below the detection limit, so the selectivity was greater than 42,000. Table 2 illustrates the effect of permeate pressure on $CO_2/CH_4$ separation at a feed pressure of 3.1 MPa and a temperature of 295 K for an $NH_3$-treated SAPO-34 membrane. For the permeate pressures tested, the $CH_4$ permeate concentration was still below the detection limit, so the selectivity was greater than 42,000. Table 3 illustrates the effect of $CO_2$ fed concentration on $CO_2/CH_4$ separation at a feed pressure of 3.1 MPa, permeate pressure of 84 kPa, and a temperature of 295 K for an $NH_3$-treated SAPO-34 membrane. The membrane was selective for $CO_2$ feed concentrations from 25% to 70%.

TABLE 1

Effect of temperature on $CO_2/CH_4$ separation*

| Temperature (K) | Permeate pressure (kPa) | $CO_2$ permeance $\times 10^8$ (mol/$m^2 \cdot$ s $\cdot$ Pa) | $CO_2/CH_4$ selectivity |
|---|---|---|---|
| 297 | 84 | 5.1 | >42,000 |
| 323 | 84 | 5.4 | >42,000 |
| 323 | 430 | 4.9 | >42,000 |

*Feed pressure: 3.1 MPa

TABLE 2

Effect of permeate pressure on $CO_2/CH_4$ separation*

| Permeate pressure (kPa) | $CO_2$ permeance $\times 10^8$ (mol/$m^2 \cdot$ s $\cdot$ Pa) | $CO_2/CH_4$ selectivity |
|---|---|---|
| 84 | 5.1 | >42,000 |
| 430 | 4.4 | >42,000 |
| 770 | 4.4 | >42,000 |

*Feed pressure: 3.1 MPa, temperature: 295 K

TABLE 3

Effect of $CO_2$ feed concentration on $CO_2/CH_4$ separation*

| $CO_2$ feed Concen. (mol %) | $CO_2$ permeance $\times 10^8$ (mol/m² · s · Pa) | $CO_2/CH_4$ Selectivity |
|---|---|---|
| 25 | 7.9 | >42,000 |
| 36 | 5.4 | >42,000 |
| 50 | 5.1 | >42,000 |
| 70 | 4.3 | >42,000 |

*Feed pressure: 3.1 MPa, permeate pressure: 84 kPa, temperature: 295 K

Figure 9:
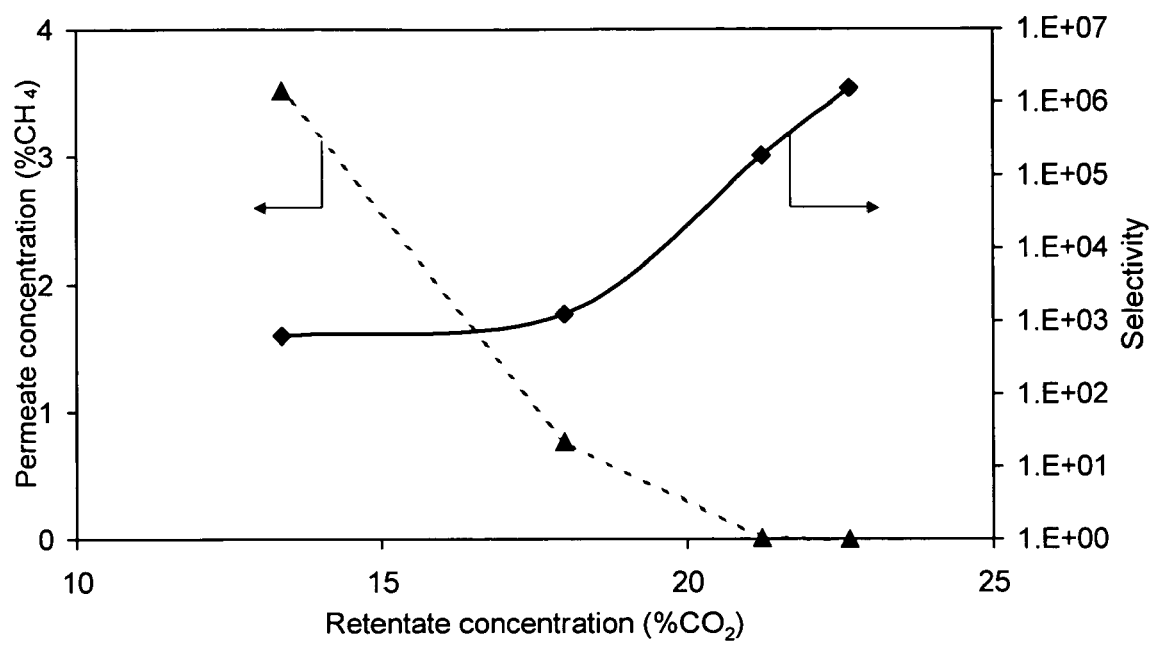
FIG. 9 illustrates the effect of $CO_2$ retentate concentration on $CH_4$ permeate concentration and $CO_2/CH_4$ selectivity for a $NH_3$ modified SAPO-34 membrane. Temperature=295 K, feed pressure=0.77 MPa, and permeate pressure=0.08 MPa.

The effects of varying the feed concentration at lower $CO_2$ feed concentrations were further investigated. FIG. 9 shows $CH_4$ permeate concentration and $CO_2/CH_4$ separation selectivity as a function of $CO_2$ retentate concentration (Temperature=295 K, feed pressure=0.77 MPa, and permeate pressure=0.08 MPa) for an $NH_3$-modified SAPO-34 membrane. Note that $CO_2$ concentration in the retentate was lower than that in the feed because $CO_2$ preferentially permeates through the membrane. Higher $CO_2$ retentate concentration resulted in greater $CO_2$ coverage in the membrane and hence more effective blocking of the permeation of $CH_4$. Thus, at higher $CO_2$ coverages, the $CH_4$ concentration in the permeate decreased resulting in greater $CO_2/CH_4$ selectivity (FIG. 9). At 295 K and a feed pressure of 0.77 MPa, the $CO_2$ retentate concentration of 23%, which corresponds to a feed concentration of 25% $CO_2$, blocked $CH_4$ to a permeate concentration below the detection limit of 36 ppm.

Figure 10:
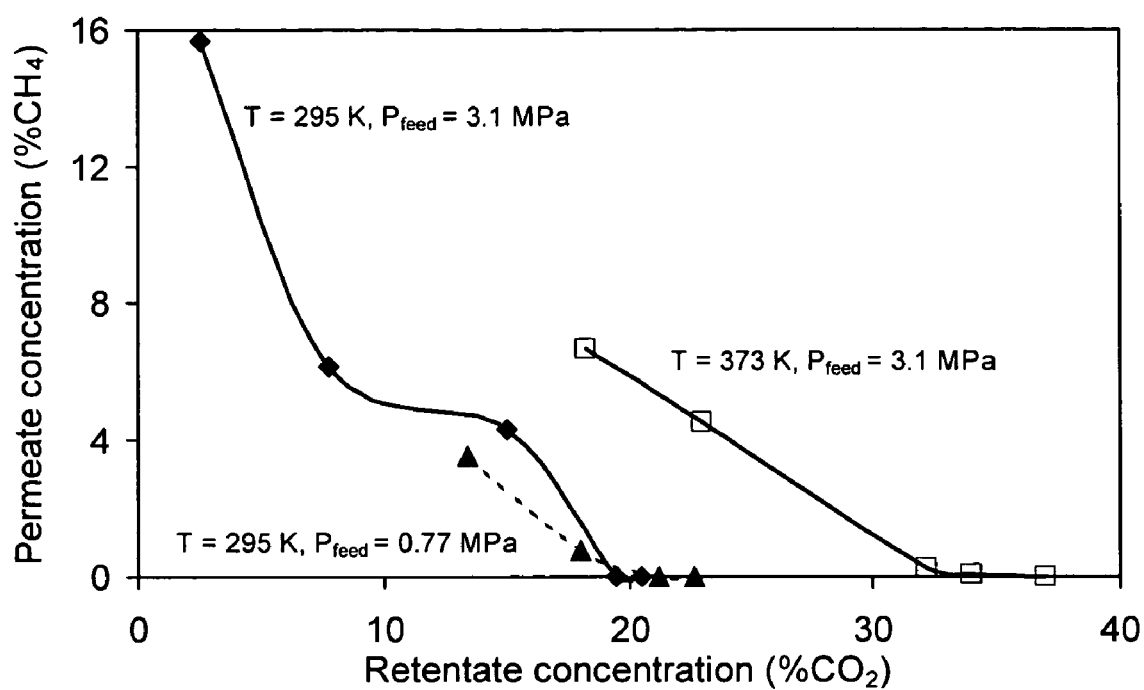
FIG. 10 illustrates the effects of $CO_2$ retentate concentration on $CH_4$ permeate concentration for a $NH_3$ modified SAPO-34 membrane. The permeate pressure was 0.08 MPa

The experiment was also performed at 3.1 MPa. At this pressure, 25% $CO_2$ feed also reduced the $CH_4$ concentration in the permeate to below 36 ppm. FIG. 10 compares the effects of $CO_2$ retentate concentration on $CH_4$ permeate concentration for ammonia modified SAPO-34 membranes at different temperatures and feed pressures. Increasing the temperature to 373 K at 3.1 MPa required 42% $CO_2$ in the feed to block $CH_4$ to permeate concentration below 36 ppm (FIG. 10).

Low feed flow rates were used to investigate the enrichment of $CH_4$ in the retentate. Lowering the flow of feed gas causes a greater concentration gradient across the length of the membrane, thereby simulating a longer membrane. Table 4 shows runs of mixtures with flow rate decreasing from 1000 to 166 mL/min at roughly equimolar feed concentration for an $NH_3$-modified SAPO-34 membrane. In each of these cases, $CH_4$ in the permeate was below the detection limit. At 166 mL/min the retentate was enriched from 53.5% CO2 in the feed to 85.6% with virtually no loss of $CH_4$.

TABLE 4

Enrichment of $CH_4$ in retentate at 3 MPa feed pressure, 0.4 MPa permeate pressure, and 323 K

| Feed flow rate | Concentration (% $CH_4$) | | |
|---|---|---|---|
| (mL/min) | Feed | Permeate | Retentate |
| 1000 | 49.9 | <36 ppm | 53.9 |
| 400 | 49.2 | <36 ppm | 59.5 |
| 200 | 55.4 | <36 ppm | 81.4 |
| 166 | 53.5 | <36 ppm | 85.6 |

Figure 11:
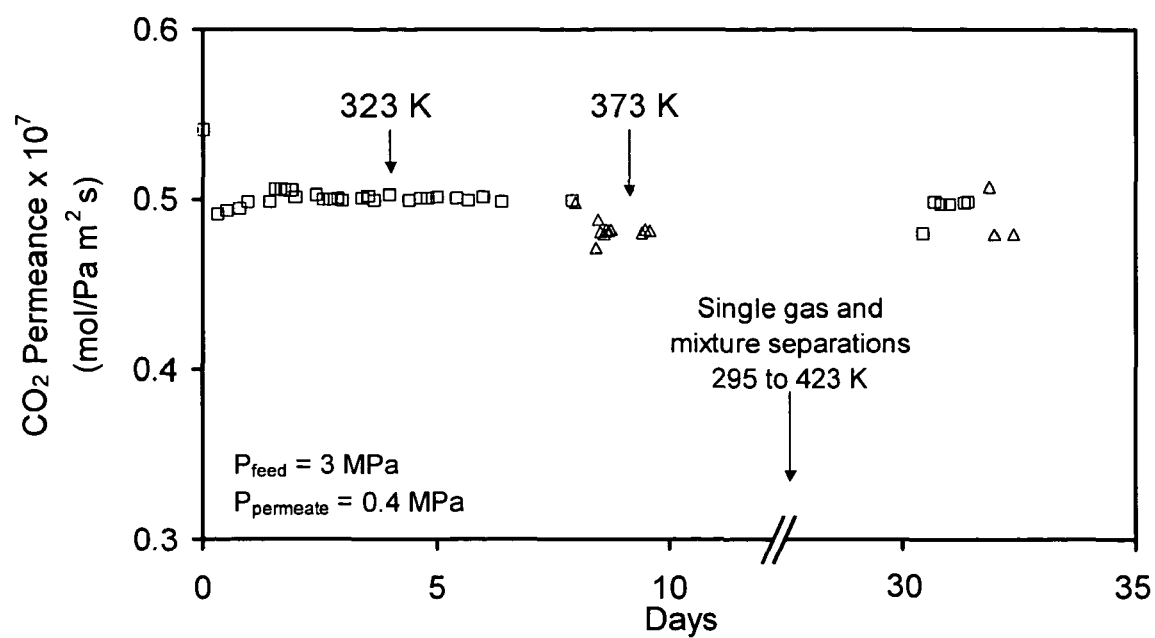
FIG. 11 shows $CO_2$ permeance at 323 K and 373 K at 3 MPa feed pressure and 0.4 MPa permeate pressure for a $NH_3$ modified SAPO-34 membrane.

A SAPO-34 membrane was $NH_3$ treated on Jun. 14, 2004 as described in Example 2 and was subsequently characterized for several days. $CO_2/CH_4$ separation began on Jun. 19, 2004. FIG. 11 shows a plot of $CO_2$ permeance over the following 32 days. The membrane was stable for 8 days when operated at 3 MPa feed pressure, 0.4 MPa permeate pressure, and 323 K. The membrane was also stable for 2 days when the temperature was increased to 373 K. At both temperatures, the $CH_4$ permeate concentrations were below 36 ppm, so the selectivities were higher than $4 \times 10^4$. The membrane exhibited repeatability when these initial conditions were restored on day 30. In FIG. 11, the measurements at 373 K are indicated by triangles.

Untreated H-SAPO-34 membranes have shown to separate other mixtures listed in Table 5 (the measurements in Table 5 were obtained for a membrane prepared on both sides of a stainless steel tube). Table 6 shows the separation selectivities for $N_2/CH_4$ and $CO_2/N_2$ mixtures through the $NH_3$ treated SAPO-34 membrane (this membrane was prepared on one side (inside) of a stainless steel tube).

TABLE 5

Mixture separation selectivities for various gas mixtures through untreated SAPO-34 membrane (84 kPa permeate pressure and 138 kPa pressure drop).

| Gas mixtures | Temperature (K) | Ideal Selectivity* | Separation selectivity** |
|---|---|---|---|
| $H_2/CH_4$ | 297 | 41 | 35 |
| $H_2/N_2$ | 473 | 7.9 | 8.1 |
| $H_2/CO_2$ | 473 | 2.3 | 1.7 |
| $H_2/CO$ | 473 | 6.7 | NM |
| $H_2/n-C_4H_{10}$ | 473 | >330 | NM*** |
| $CO_2/N_2$ | 297 | 20 | NM |
| $N_2/CH_4$ | 297 | 6.5 | NM |

*Ideal selectivity: the ratio of single gas permeances
**Separation selectivity: the ratio of the permeances for mixtures (50/50)
***NM: not measured

TABLE 6

Mixture separation selectivities at 295 K for 50/50 $N_2/CH_4$ and $CO_2/N_2$ mixtures through $NH_3$ treated SAPO-34 membrane (84 kPa permeate pressure and 138 kPa pressure drop).

| Gas mixtures | Separation selectivity** |
|---|---|
| $CO_2/N_2$ | 6 |
| $N_2/CH_4$ | 5 |

We claim:

1. A method for separating a first gas component from a gas mixture containing at least a first and a second gas component, the method comprising the steps of:
   providing a modified molecular sieve membrane, the membrane having a feed and a permeate side, being selectively permeable to the first gas component over the second gas component, and being modified by adsorption of a modifying agent within the zeolite pores of the membrane, wherein the modifying agent does not irreversibly react with the molecular sieve;
   applying a feed stream including the first and the second gas components to the feed side of the membrane;
   providing a driving force sufficient for permeation of the first gas component through the membrane, thereby producing a permeate stream enriched in the first gas component from the permeate side of the membrane, wherein the first gas component is carbon dioxide and the second gas component is methane.

2. The method of claim 1, wherein the modified membrane is an ammoniated supported silicoaluminophosphate-34 (SAPO-34) membrane.

3. The method of claim 1, wherein the feed stream is natural gas.

4. The method of claim 1, wherein the modifying agent is adsorbed within the membrane or both within and on the membrane.

5. The method of claim 1 wherein the molecular sieve membrane further comprises non-zeolite pores and the modifying agent also adsorbs in the non-zeolite pores.

6. The method of claim 1, wherein the molecular sieve membrane is a silicoaluminophosphate (SAPO) membrane.

7. The method of claim 6, wherein the membrane is SAPO-34.

8. The method of claim 1 wherein the molecular sieve membrane comprises Brønsted acid sites and the modifying agent adsorbs at said acid sites.

9. The method of claim 1, wherein the modifying agent is ammonia or an amine.

10. The method of claim 1, wherein the modifying agent is ammonia.

* * * * *